(12) United States Patent
Kamoi

(10) Patent No.: US 9,921,146 B2
(45) Date of Patent: Mar. 20, 2018

(54) PIPELINE MANAGEMENT SUPPORTING SERVER AND PIPELINE MANAGEMENT SUPPORTING SYSTEM

(71) Applicant: Atsushi Kamoi, Tokyo (JP)

(72) Inventor: Atsushi Kamoi, Tokyo (JP)

(73) Assignee: NEC Corporation, Tokyo (JP)

( * ) Notice: Subject to any disclaimer, the term of this patent is extended or adjusted under 35 U.S.C. 154(b) by 502 days.

(21) Appl. No.: 14/375,886

(22) PCT Filed: Dec. 28, 2012

(86) PCT No.: PCT/JP2012/084048
§ 371 (c)(1),
(2) Date: Jul. 31, 2014

(87) PCT Pub. No.: WO2013/145493
PCT Pub. Date: Oct. 3, 2013

(65) Prior Publication Data
US 2015/0046099 A1    Feb. 12, 2015

(30) Foreign Application Priority Data

Mar. 30, 2012  (JP) .................................. 2012-083205

(51) Int. Cl.
*G01B 3/44*  (2006.01)
*G01N 19/08*  (2006.01)
(Continued)

(52) U.S. Cl.
CPC .............. *G01N 19/08* (2013.01); *G01F 1/05* (2013.01); *G01H 17/00* (2013.01); *G01M 3/243* (2013.01);
(Continued)

(58) Field of Classification Search
CPC ................................ G01N 19/08; G01M 3/243
See application file for complete search history.

(56) References Cited

U.S. PATENT DOCUMENTS 5,571,966 A * 11/1996 Tsuboi ................. G01M 7/025
702/34
6,567,006 B1   5/2003 Lander et al.
(Continued)

FOREIGN PATENT DOCUMENTS

| EP | 2 194 535 A1 | 6/2010 |
| JP | 2-81299 | 3/1990 |

(Continued)

OTHER PUBLICATIONS

International Search Report dated Feb. 5, 2013.
(Continued)

*Primary Examiner* — Matthew G Marini
(74) *Attorney, Agent, or Firm* — Finnegan, Henderson, Farabow, Garrett & Dunner, L.L.P.

(57) ABSTRACT

The present invention provides a pipeline management supporting server capable of unifying management of attribute data of a pipe component and location information on a pipe network, efficiently detecting an abnormality of a pipeline remotely, and diagnosing the degradation state of the pipeline. The pipeline management supporting server (1) of the present invention includes: a private data processing unit (11) and a statistical calculation processing unit (12). The private data processing unit (11) includes an event data acquisition section (114) that acquires event data of a pipeline measured by a sensor(s), a measured event data storage section (112) that stores the event data of the pipeline, a pipeline database data storage section (111) that stores pipeline database data, a possible abnormality detection section (113), and an information output section (115). The possible abnormality detection section (113) identifies a pipeline and a location pertaining to the acquired event data of the pipeline with reference to the pipeline database data (Continued)

stored in the pipeline database data storage section (111) and generates possible abnormality detection information on the acquired event data of the pipeline. The statistical calculation processing unit (12) includes a data analysis section (122) and a statistical calculation data storage section (121) that stores statistical calculation data. The data analysis section (122) prepares, from event data of plural pipelines each having the same attribute as the pipeline pertaining to the event data acquired by the private data processing unit (11), an aging characteristic graph of the plural pipelines. The statistical calculation data storage section (121) stores the aging characteristic graph prepared by the data analysis section (122). The data analysis section (122) further generates degradation state diagnostic information on the pipeline by checking the pipeline pertaining to the event data acquired by the private data processing unit (11) against the aging characteristic graph. The information output section (115) of the private processing unit (11) outputs the degradation state diagnostic information and abnormality determination result detection information that is generated by examining the possible abnormality detection information and the degradation state diagnostic information in comparison.

7 Claims, 7 Drawing Sheets

(51) Int. Cl.
*G06Q 50/06* (2012.01)
*G01F 1/05* (2006.01)
*G01H 17/00* (2006.01)
*G06F 17/18* (2006.01)
*G06Q 10/06* (2012.01)
*G01M 3/24* (2006.01)

(52) U.S. Cl.
CPC ........... *G06F 17/18* (2013.01); *G06Q 10/063* (2013.01); *G06Q 50/06* (2013.01)

(56) References Cited

U.S. PATENT DOCUMENTS

| 2004/0093174 A1 | 5/2004 | Lander |
| 2012/0007743 A1* | 1/2012 | Solomon ............... G01M 3/243 340/605 |

FOREIGN PATENT DOCUMENTS

| JP | 8-96039 | 4/1996 |
| JP | 2000-259222 | 9/2000 |
| JP | 2003-345927 | 12/2003 |
| JP | 2005-114583 | 4/2005 |
| WO | WO 02-093279 A2 | 11/2002 |
| WO | WO 2008-103176 A1 | 8/2008 |

OTHER PUBLICATIONS

Extended European Search Report dated Oct. 2, 2015 by the European Patent Office in counterpart European Patent Application No. 12872855.7.

English-language European Office Action dated Nov. 30, 2017, from the European Patent Office in counterpart European Patent Application 12872855.7, dated Nov. 30, 2017.

\* cited by examiner

| Type of pipe | | | Diameter (mm) |
|---|---|---|---|
| DIP | Ductile iron pipe | Earthquake-resistant pipe with polyethylene sleeve | 700 or more |
| | | | 400 or more |
| | | | 300 or less |
| | | With polyethylene sleeve | 700 or more |
| | | | 400 or more |
| | | | 300 or less |
| | | Without polyethylene sleeve | 700 or more |
| | | | 400 or more |
| | | | 300 or less |
| SP | Steel pipe | | 700 or more |
| | | | 400 or more |
| | | | 300 or less |
| CIP | Cast-iron pipe | High-quality cast-iron pipe | 700 or more |
| | | | 400 or more |
| | | | 300 or less |
| HIVP | Impact-resistant rigid vinyl chloride pipe | | 50 |
| VLGP | Rigid vinyl chloride lined steel pipe (with polysleeve) | | 50 |
| | Rigid vinyl chloride lined steel pipe (without polysleeve) | | 50 |

FIG. 4

PIPELINE MANAGEMENT SUPPORTING SERVER AND PIPELINE MANAGEMENT SUPPORTING SYSTEM

CROSS-REFERENCE TO RELATED PATENT APPLICATIONS

This application is a National Stage Entry of International Application No. PCT/JP2012/084048, filed Dec. 28, 2012, which claims priority from Japanese Patent Application No. 2012-083205, filed Mar. 30, 2012. The entire contents of the above-referenced applications are expressly incorporated herein by reference.

TECHNICAL FIELD

The present invention relates to a pipeline management supporting server and a pipeline management supporting system.

BACKGROUND ART

As a technique of managing pipelines such as a water supply pipeline and the like, there is an management database mapping system in which a pipeline database and a map are combined. The pipeline database is a collection of attribute data (the type of pipe, the diameter, the installation year, and the like) of pipe components configuring a pipeline. The map shows a location of a pipe network of the pipeline. In the management database mapping, the attribute data of a pipe component configuring a pipeline and the location information data of a pipe network can be uniformly managed and can be shown by superimposing them on the map. On the other hand, as maintenance of the pipeline, for example, there is a water-leakage detection in a water supply pipeline. Examples of the water-leakage detection include a measurement at plural locations by loggers, a measurement at two locations and correlation analysis between them, and a measurement of sound. Among them, the measurement of sound is performed as follows. A skilled worker goes to a site in the midnight with little noise to detect a water-leakage sound from the surface of the ground, a manhole, or the like. Moreover, in order to maintain and manage a water supply pipeline network, a system in which a flow rate measurement device, a pressure measurement device, or a vibration measurement device is attached to a target pipeline, collected measurement data are sent to a remote central processing center, and an abnormality such as a water-leakage is detected on the basis of the measurement data has been proposed (Patent Document 1).

PRIOR ART DOCUMENT

Patent Document

Patent Document 1: JP H8-96039 A

SUMMARY OF INVENTION

Problem to be Solved by the Invention

In the conventional management database mapping system, although attribute data of a pipe component and location information on a pipe network can be uniformly managed, an abnormality of a pipeline cannot be detected. Moreover, in the conventional technique of detecting a water-leakage and the like, the detection is performed on site, skilled workers are required specifically for the measurement of sound, and the operation of the measurement is complicated. That is to say, the conventional technique is not efficient. In contrast, in the system proposed in the Patent Document 1, attribute data of a pipe component and location information on a pipe network can be uniformly managed, and further, an abnormality of a pipeline can be detected remotely. That is to say, the system of Patent Document 1 is efficient. Although the detection of a water-leakage is important, it is further required to predict an abnormality such as a water-leakage in advance from the viewpoint of limited water resources, economy, and prevention of disasters caused by a cave in the road and the like by a water-leakage. However, in the system of the Patent Document 1, although an abnormality can be detected, the degradation state of a pipeline cannot be diagnosed. Such problem occurs not only in management of water supply pipeline networks but also in pipeline networks of plants and energy-related facilities such as pipelines of oil and gas and the like.

Hence, the present invention is intended to provide a pipeline management supporting server and a pipeline management supporting system, capable of unifying management of attribute data of a pipe component and location information on a pipe network, efficiently detecting an abnormality of a pipeline remotely, and diagnosing the degradation state of the pipeline.

Means for Solving Problems

In order to achieve the aforementioned objects, the pipeline management supporting server of the present invention is a pipeline management supporting server including: a private data processing unit; and a statistical calculation processing unit, wherein the private data processing unit includes: an event data acquisition section that acquires event data of a pipeline measured by at least one sensor; a measured event data storage section that stores the event data of the pipeline; a pipeline database data storage section that stores pipeline database data; a possible abnormality detection section; and an information output section, wherein the possible abnormality detection section identifies a pipeline and a location pertaining to the acquired event data of the pipeline with reference to the pipeline database data stored in the pipeline database data storage section and generates possible abnormality detection information on the acquired event data of the pipeline, the statistical calculation processing unit includes: a data analysis section; and a statistical calculation data storage section that stores statistical calculation data, wherein the data analysis section prepares, from event data of plural pipelines each having the same attribute as the pipeline pertaining to the event data acquired by the private data processing unit, an aging characteristic graph of the plural pipelines, the statistical calculation data storage section stores the aging characteristic graph prepared by the data analysis section, the data analysis section further generates degradation state diagnostic information on the pipeline pertaining to the event data acquired by the private data processing unit by checking the pipeline against the aging characteristic graph, and the information output section of the private data processing unit outputs the degradation state diagnostic information and abnormality determination result detection information that is generated by examining the possible abnormality detection information and the degradation state diagnostic information in comparison.

The pipeline management supporting system of the present invention is a pipeline management supporting system including: a pipeline management supporting server; at least one sensor; an operation display device; at least one data collection transmission terminal; and a communication network, wherein the pipeline management supporting server is the pipeline management supporting server according to the present invention, event data measured by the at least one sensor are sent to the pipeline management supporting server by the at least one data collection transmission terminal through the communication network, and abnormality determination result detection information and degradation state diagnostic information output from the pipeline management supporting server are acquirable by the operation display device via the communication network.

Effects of the Invention

The present invention makes it possible to uniformly manage attribute data of a pipe component and location information on a pipe network, efficiently detect an abnormality of a pipeline remotely, and diagnose the degradation state of the pipeline.

BRIEF DESCRIPTION OF DRAWINGS

FIG. 4 is an explanatory drawing showing an example of management database data in an example of the present invention.

DESCRIPTION OF EMBODIMENTS

In the pipeline management supporting server of the present invention, as substitute for generating an aging characteristic graph by the data analysis section, the statistical calculation data storage section may include a previously-prepared aging characteristic graph of pipelines each having the same attribute as the pipeline pertaining to the event data acquired by the private data processing unit, and the data analysis section may generate degradation state diagnostic information on the pipeline pertaining to the event data acquired by the private data processing unit by checking the pipeline against the previously-prepared aging characteristic graph.

In the pipeline management supporting server of the present invention, it is preferred that the statistical calculation processing unit further includes a calculation processing correction section, and the calculation processing correction section updates the aging characteristic graph on the basis of the acquired event data.

In the statistical calculation processing unit of the pipeline management supporting server of the present invention, it is preferred that the data analysis section further extracts disturbance energy data included in the event data and prepares a disturbance energy characteristic graph on the basis of the disturbance energy data.

In the statistical calculation processing unit of the pipeline management supporting server of the present invention, it is preferred that the degradation state diagnostic information generated by the data analysis section is at least one of degradation index evaluation information and soundness index evaluation information on the pipeline.

In a preferred aspect of the pipeline management supporting server of the present invention, the at least one sensor includes at least one vibration sensor, and the event data include vibration data acquired by the at least one vibration sensor is preferable. In this aspect, it is preferred that the at least one sensor further includes at least one flow rate sensor, and the event data include flow rate data acquired by the at least one flow rate sensor.

In the pipeline management supporting server of the present invention, the pipeline to be managed preferably is a water supply pipeline.

The embodiment of the present invention is described below. The following embodiment, however, is merely an example of the present invention, and the present invention is not at all limited by the following embodiment.

Figure 1:
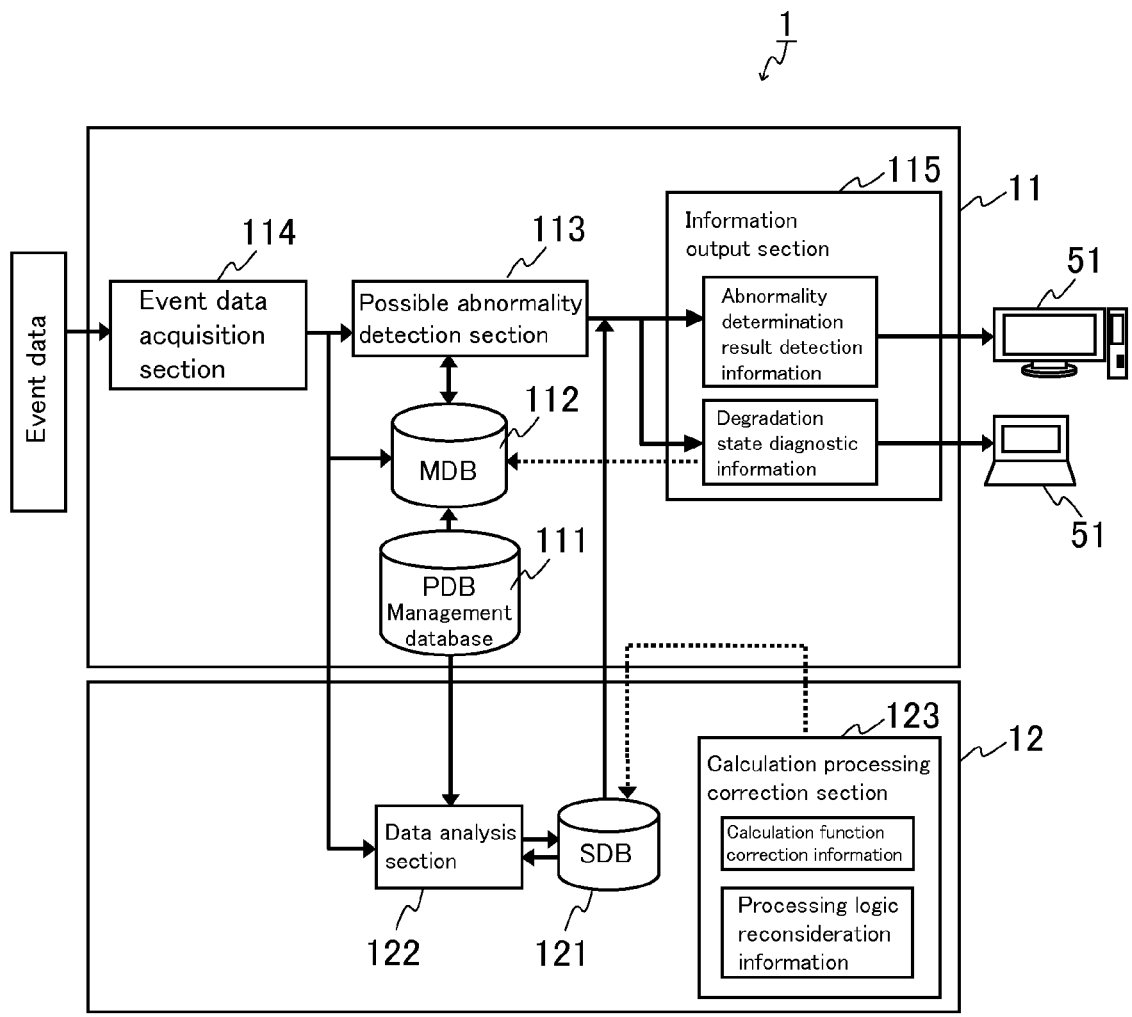
FIG. 1 is a block diagram showing a configuration of an example of the pipeline management supporting server according to the present invention.
Figure 2:
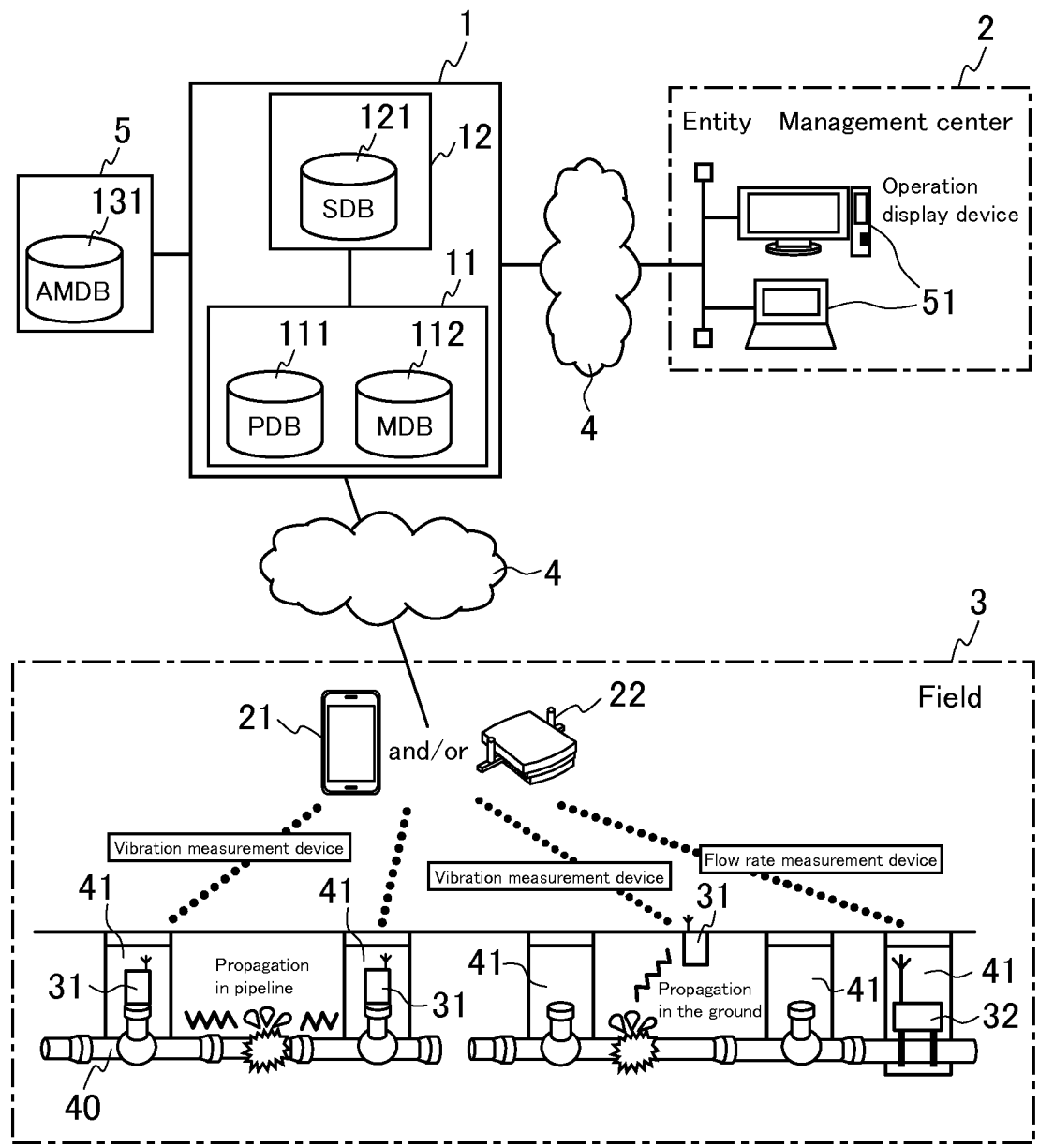
FIG. 2 is an explanatory drawing showing a configuration of an example of the pipeline management supporting system according to the present invention.

FIG. 1 is a block diagram showing an example of a configuration of the pipeline management supporting server according to the present invention. FIG. 2 is an example of a configuration of the pipeline management supporting system according to the present invention. The present embodiment is described with reference to, as an example, the case where a pipeline to be managed is a water supply pipeline. In FIGS. 1 and 2, the identical parts are denoted by identical reference numerals.

(Pipeline Management Supporting System)

As shown in FIG. 2, this pipeline management supporting system includes a pipeline management supporting server 1, a vibration sensor(s) (vibration measurement device(s)) 31 and a flow rate sensor(s) (flow rate measurement device(s)) 32 as the at least one sensor, an operation display device (client PC) 51 arranged in a management center 2 of a business entity, and a mobile terminal 21 and/or a fixed relay station 22 as the at least one data collection transmission terminal. The flow rate sensor(s) 32 is an optional component, may not be included, and is preferably included. The client PC 51 is, for example, a PC in the Waterworks Bureau of each municipality. An asset management system 5 is connected to the pipeline management supporting server 1. The asset management system 5 includes an asset management database data storage section (AMDB) 131. In this pipeline management supporting system, the pipeline management supporting server 1 is connected to the mobile terminal 21 and/or the fixed relay station 22 in a field 3 and the operation display device 51 in the management center 2 via a communication network 4. The communication network 4 is not particularly limited, and a conventionally known communication network can be used. The communication network 4 may be a wired communication network or a wireless communication network, and examples thereof include a telephone network, the Internet, and LAN (local-area network).

(Pipeline Management Supporting Server 1)

The pipeline management supporting server 1 is, for example, arranged in a data center (operated in the cloud environment), collects data (vibration data and flow rate data) measured by many vibration measurement devices 31 (and flow rate measurement devices 32) in plural business entities via a mobile terminal 21 and/or a fixed relay station 22, and outputs processing results such as an abnormality detection, a function correction, the degradation state, and the like to an operation display device 51 as the degradation state diagnostic information and abnormality determination result detection information that is generated by examining the possible abnormality detection information and the degradation state diagnostic information in comparison. The vibration data and the flow rate data correspond to the "event data" of the present invention.

As shown in FIGS. 1 and 2, the pipeline management supporting server 1 includes a private data processing unit 11 and a statistical calculation processing unit 12 as main components. The private data processing unit 11 includes a pipeline database data storage section (PDB) 111, a measured event data storage section (MDB) 112, a possible abnormality detection section 113, an event data acquisition section 114, and an information output section 115. The statistical calculation processing unit 12 includes a statistical calculation data storage section (SDB) 121 and a data analysis section 122 and further includes a calculation processing correction section 123. The calculation processing correction section 123 is an optional component, may not be included, and is preferably included. The event data acquisition section 114 is connected to the MDB 112, the possible abnormality detection section 113, and the data analysis section 122. The PDB 111 is connected to the MDB 112 and the data analysis section 122. The MDB 112 is connected to the possible abnormality detection section 113. The possible abnormality detection section 113 is connected to the information output section 115. The information output section 115 is connected to the MDB 112. The data analysis section 122 is connected to the SDB 121. The SDB 121 is connected to the information output section 115. The calculation processing correction section 123 is connected to the SDB 121.

(Private Data Processing Unit 11)

The private data processing unit 11 generates abnormality determination result detection information. Specifically, in the private data processing unit 11, the event data acquisition section 114 acquires vibration data and flow rate data (event data) of a pipeline, measured by the vibration sensor(s) 31 and the flow rate sensor(s) 32. The MDB 112 stores the event data. The PDB 111 stores a pipeline database data. The possible abnormality detection section 113 identifies a pipeline and a location pertaining to the acquired event data with reference to the pipeline database data. The possible abnormality detection section 113 generates possible abnormality detection information on the acquired event data by time correlation analysis such as an invariant analysis technique. The determination of abnormality or normality is performed by examining this possible abnormality detection information and degradation state diagnostic information that is generated by the data analysis section 122 in the statistical calculation processing unit 12 described below in comparison. By the determination, the abnormality determination result detection information is generated. Afterward, the information output section 115 outputs the abnormality determination result detection information and the degradation state diagnostic information to the operation display device 51.

(Statistical Calculation Processing Unit 12)

The statistical calculation processing unit 12 is intended to improve the accuracy of a citation function as interpolation of the statistical calculation, the determination logic, and the like. In order to handle more event data (measurement data such as vibration data and flow rate data), measurement data on each business entity are collected, and on the basis of the measurement data, the statistical calculation processing is performed. Afterward, the results of the statistical calculation are reflected to private processing for each business entity. In the statistical calculation processing unit 12, the data analysis section 122 prepares, from event data on plural (preferably many) pipelines each having the same attribute as the pipeline pertaining to the event data acquired by the private data processing unit 11, an aging characteristic graph of the plural pipelines. The statistical calculation data storage section 121 stores statistical calculation data and the aging characteristic graph prepared by the data analysis section 122. The data analysis section 122 further generates degradation state diagnostic information on the pipeline pertaining to the event data acquired by the private data processing unit 11 by checking the pipeline against the aging characteristic graph. In the pipeline management supporting server 1, as substitute for generating an aging characteristic graph by the data analysis section 122, the statistical calculation data storage section 121 may include a previously-prepared aging characteristic graph of pipelines each having the same attribute as the pipeline pertaining to the event data acquired by the private data processing unit 11, and the data analysis section 122 may generate degradation state diagnostic information on the pipeline pertaining to the event data acquired by the private data processing unit 11 by checking the pipeline against the previously-prepared aging characteristic graph. The calculation processing correction section 123 updates the aging characteristic graph on the basis of the event data acquired by the private data processing unit 11.

(Management Center 2)

The management center 2 can be, for example, a management center in the Waterworks Bureau of each municipality. The operation display device (client PC) 51 is, as mentioned above, arranged in the management center 2 of each business entity. The operation display device 51 performs request operations of various processes for the pipeline management supporting server 1 and acquires and displays the results of the calculation processing and the like from the pipeline management supporting server 1. The results of the calculation processing includes the degradation state diagnostic information and abnormality determination result detection information that is generated by examining the possible abnormality detection information and the degradation state diagnostic information in comparison and are specifically described below. The operation display device 51 includes an operation unit such as a keyboard or a mouse and a display unit such as a display. The operation display device 51 can perform plural connected operations to the pipeline management supporting server 1.

(Field 3)

In the field 3, the vibration sensor(s) 31 is arranged in a water supply pipeline 40 in a manhole 41 or on the road or the surface of the ground immediately above the water supply pipeline 40 (vibration propagation under the ground). A sensor number is given for the vibration sensor(s) 31. The flow rate sensor(s) 32 is arranged in the water supply pipeline 40 in the manhole 40. The vibration sensor(s) 31 is, for example, a high-sensitivity vibration sensor(s) (e.g., a vibration sensor with a voltage sensitivity: about 20 mV/(m/s$^2$) and the minimum detection acceleration: about 0.01 m/s$^2$) and contains a processing circuit that performs A/D conversion, primary filtering processing, and the like, a battery, a short-range wireless module, and the like. The flow rate sensor(s) 32 is utilized and connected for the purpose of requiring a measurement device(s) other than the vibration sensor(s) to detect a water-leakage or predict degradation. The flow rate sensor(s) 32 can be, for example, an ultrasonic flow rate sensor(s) or the like. Such flow rate sensor can be arranged by a method capable of attaching the flow rate sensor(s) afterward without requiring boring a pipe component of a pipeline and processing such as cutting and the like. The accuracy of the vibration sensor(s) 31 is reduced in some cases by air bubbles, contaminations, and the like. In order to prevent this reduction, it is preferable to use the vibration sensor(s) 31 and the flow rate sensor 32 in combination.

The mobile terminal 21 and/or the fixed relay station 22 functions as the data collection transmission terminal(s). That is, the mobile terminal 21 and/or the fixed relay station 22 receives vibration data or flow rate data measured by plural vibration sensors (vibration measurement devices) 31 or plural flow rate sensors (flow rate measurement devices) 32 through a short-range wireless communication. The mobile terminal 21 and/or the fixed relay station 22 sends the received vibration data or the received flow rate data to the pipeline management supporting server 1 through the communication network 4. The mobile terminal 21 and/or the fixed relay station 22 may subject the received vibration data or the received flow rate data to secondary processing, for example, before sending, so that the received vibration data or the received flow rate data become transmittable. The mobile terminal 21 may receive results of the processes in the pipeline management supporting server 1 and may have a display function which enables the mobile terminal 21 to find out the state of a water-leakage or the like at a site, for example.

(Asset Management System 5)

The asset management system 5 includes the AMDB 131 as mentioned above. The AMDB 131 stores asset database data. The asset management system 5 manages data of the pipe attributes and the aging state in the asset database data, the soundness assessment by degradation checking/investigation circumstances, and the hazard assessment by the consideration of an influence of an earthquake disaster and the like, for example. The asset management system 5 is linked with the private data processing unit 11 in the pipeline management supporting server 1, for example. By this linking, on the basis of the above-mentioned data, the life cycle cost of each pipeline is estimated, and the replacement demand of a managed entire pipeline is predicted, and the life cycle cost and the replacement demand are considered by comparing with the fiscal balance outlook to support the medium- to long-term replacement/investment plan.

As mentioned above, the vibration data of the vibration measurement device(s) 31 (and the flow rate data of the flow rate measurement device(s) 32) arranged in each pipeline are collected to the pipeline management supporting server 1 regularly or as required via the mobile terminal 21 and/or the fixed relay station 22. Afterward, processes of abnormality determination result detection, a degradation evaluation, and a soundness evaluation are performed in the pipeline management supporting server 1. The results of the processes are read by and output to the operation display device 51 of the management center 2 in each business entity. Moreover, the pipeline management supporting server 1 is linked with the asset management system 5, for example, to support consideration of the medium- to long-term replacement/investment plan. The procedures of the processes in the pipeline management supporting server 1 are described below with reference to FIGS. 1 to 6B.

First, as mentioned above, measurement data are acquired by an event data acquisition section 114 (Step S1). Afterward, a pipeline and a location pertaining to the measurement data are found out by checking the sensor number of the vibration sensor against the management database by a possible abnormality detection section 113 (Step S2).

The possible abnormality detection section 113 subjects the vibration data of each vibration measurement device 31 alone to relative evaluation of acceleration variation with respect to the time axis in a characteristic frequency band of a target pipeline and performs correlation prediction analysis such as invariant analysis technique (Step SA1). By this analysis, a possible abnormality is detected (Step SA2). In both of the case where there is generation of possible abnormality (Yes) and the case where there is no generation of possible abnormality (No), the vibration data and the analysis results are stored and accumulated in the MDB 112 (Step SA3) (Private data processing).

Figure 3:
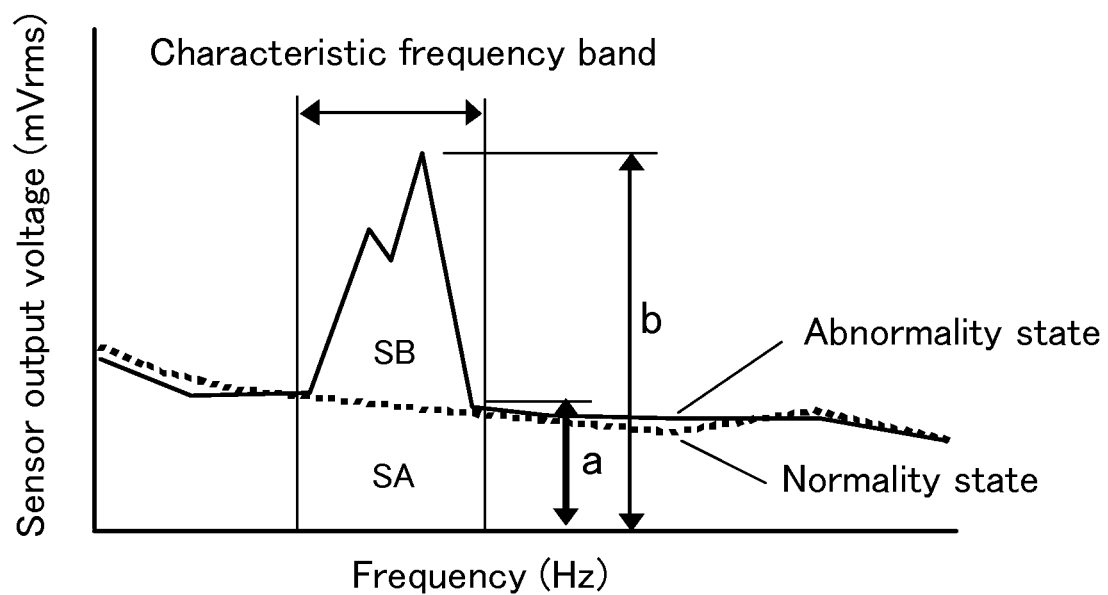
FIG. 3 is a graph showing an example of vibration data in an example of the present invention.
Figure 5:
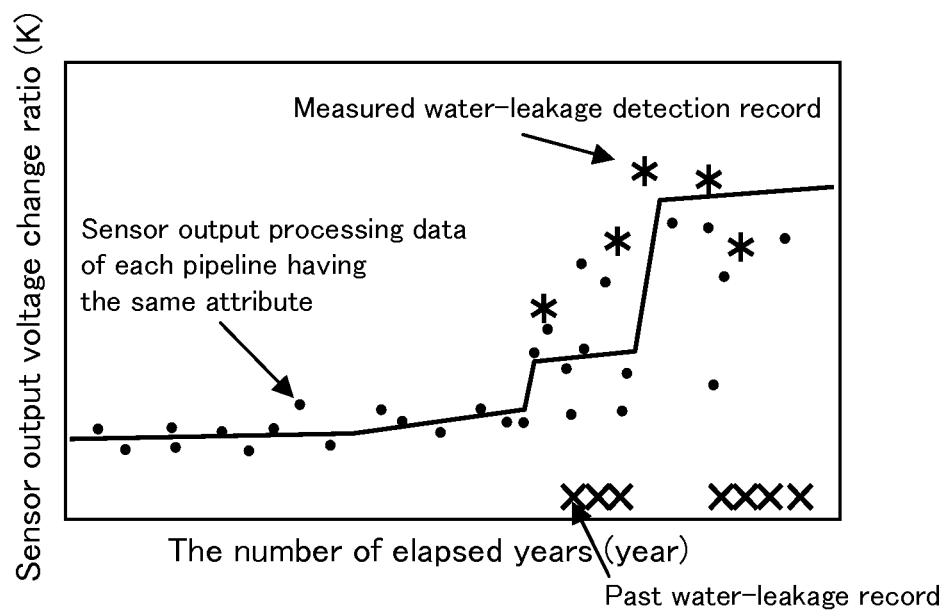
FIG. 5 is an example of an aging characteristic graph in an example of the present invention.
Figure 6A:
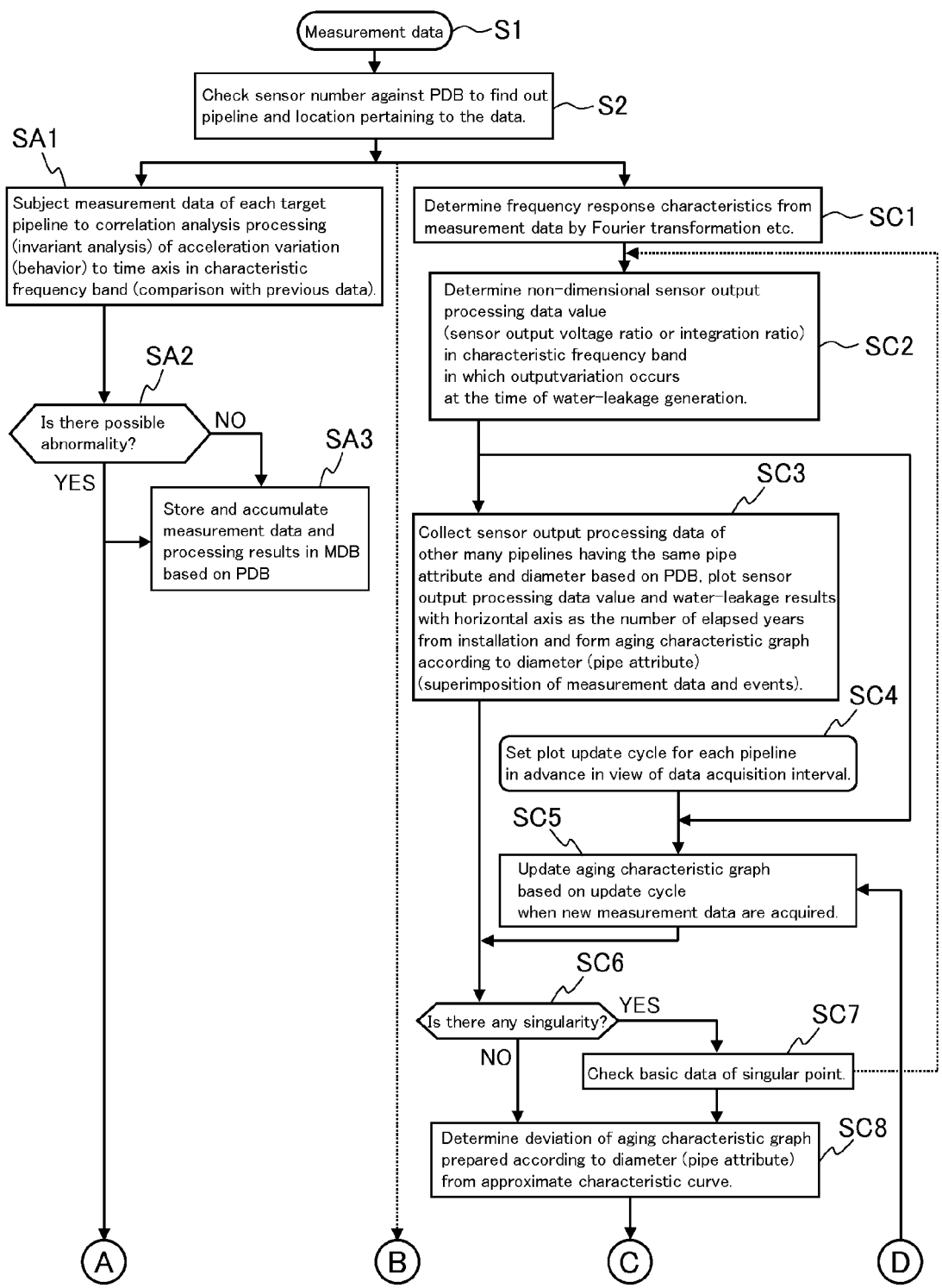
FIG. 6A is a flow chart showing an example of a processing flow in the pipeline management supporting server according to the present invention.
Figure 6B:
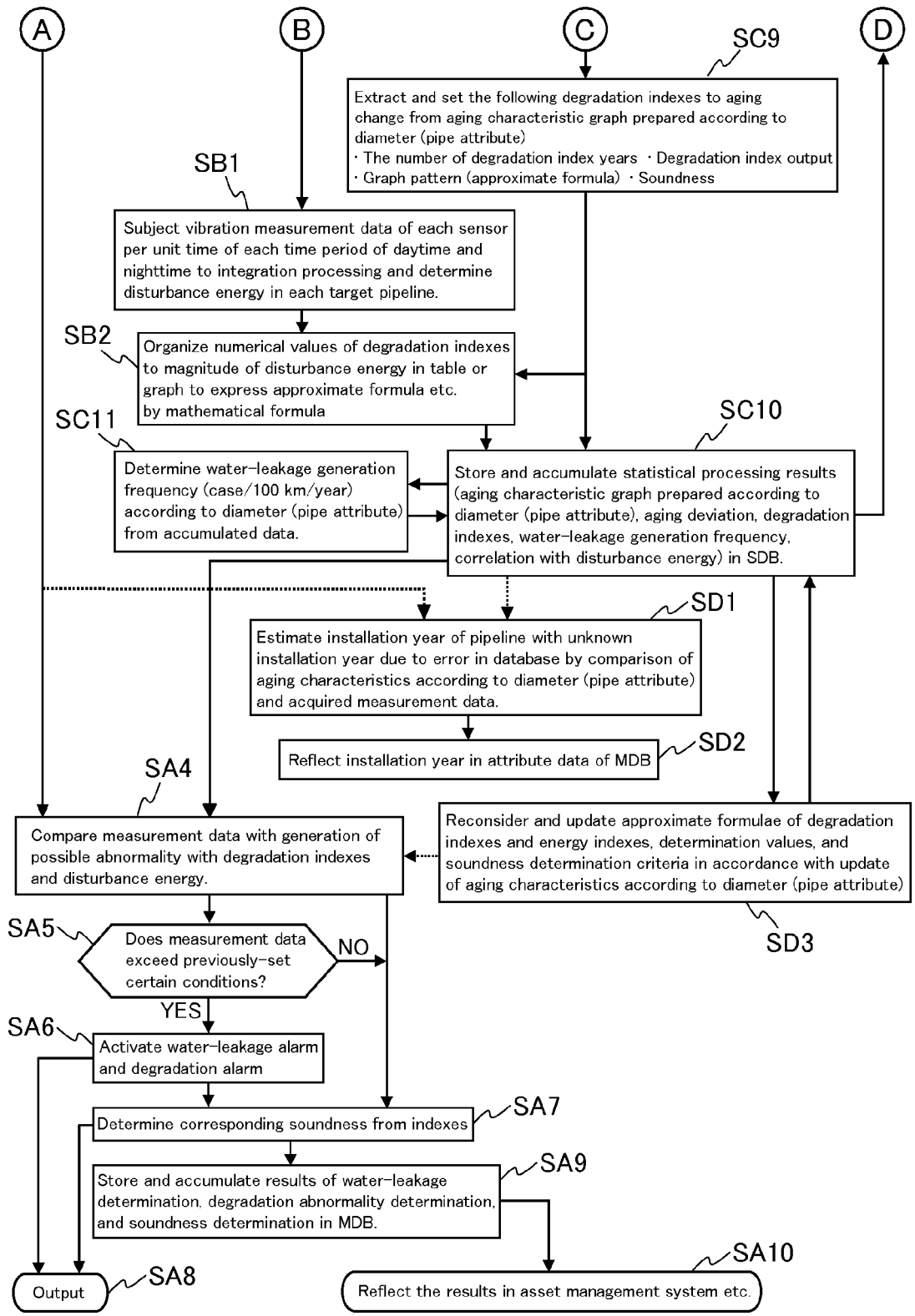
FIG. 6B is a flow chart showing another example of a processing flow in the pipeline management supporting server according to the present invention.

Aging characteristics of pipeline(s) having the same attribute as the target pipeline are obtained by statistical consideration processing based on the pipeline database data, using the data analysis section 122. Specifically, first, in the step SC1, a frequency response graph shown in FIG. 3 is determined from the measurement data by Fourier transformation or the like. In the graph, the sensor output voltage change ratio b/a=K assuming that the sensor output voltage in the normality state is a (mVrms), and the measured sensor output voltage is b (mVrms) in the characteristic frequency band of the target pipeline or the integration ratio SB/SA in the characteristic frequency band is determined as a non-dimensional sensor output processing data (Step SC2). As shown in FIG. 3, the sensor output voltage in the characteristic frequency band is increased in the abnormality state. Moreover, large amounts of measurement data of pipelines with the various numbers of elapsed years from installation are collected by pipeline attribute categories based on the pipeline database data. The pipeline attribute categories based on the pipeline database data can be, for example, pipeline attribute categories shown in FIG. 4. As shown in FIG. 4, in these pipeline attribute categories, pipelines are categorized by the type of pipe and the diameter (mm) Afterward, the sensor output processing data and the water-leakage results are plotted (the measurement data are superimposed on the real events), and for example, on the basis of the management database data categorized according to the diameter that is a pipeline attribute category shown in FIG. 4, an aging characteristic graph (aging change graph) is formed (Step SC3) (Statistical calculation processing). An example of the aging characteristic graph is shown in FIG. 5. In FIG. 5, the vertical axis indicates the sensor output voltage change ratio (K) that is the sensor output processing data, the horizontal axis indicates the number of elapsed years, "*" represents a water-leakage detection record at the time of measurement (measured water-leakage detection record), and "x" represents a past water-leakage record.

In the step SC4, in view of an interval of acquiring measurement data, a cycle of updating plots for each pipeline is previously set, and when new measurement data are acquired in the step SC5, the aging characteristic graph is updated on the basis of the update cycle.

Subsequently, in the step SC6, with respect to the circumstances of the aging characteristic graph prepared according to the diameter that is a pipeline attribute category, whether or not there is a singular point is checked, and when there is a singular point, the basic data (sensor output processing data in a characteristic frequency band) of the singular point are checked and reconsidered using the operation display element 51 (Step SC7). Moreover, in the step SC8, the deviation of the aging characteristic graph from an averaging curve (approximate characteristic curve) graph is found out according to the elapsed years (Statistical calculation processing).

Subsequently, in the step SC9, degradation indexes (the degradation index number of years, a degradation index output, a graph pattern, and the soundness) are extracted and set from the aging characteristic graph prepared according to the diameter that is a pipeline attribute category) (Statistical calculation processing). The degradation index number of years is the number of elapsed years in which a water-leakage frequency becomes high, i.e., the number of elapsed years at a point with a large variation of the sensor output processing data at around the number of elapsed years. The variation point can be extracted from a slope change by differentiation, and the number of the variation points may be plural. The degradation index output is a sensor output processing data value corresponding to the degradation index number of years. The graph pattern is a numerically converted graph shape such as the number of variation points in the sensor output processing data, an output slope change in a range of the small number of elapsed years, and the like and is preferably expressed by a mathematical formula using an approximate formula that can be partitioned. For the soundness, the number of elapsed years that is the number of elapsed years at the variation point of the final sensor output processing data or more is set as a maximum value, and three or five indexes are set in view of the number of degradation index years, the degradation index output, the variation of output by the number of elapsed years, and statutory useful life.

In the step SC10, the statistical processing results such as aging characteristics categorized according to the diameter that is a pipeline attribute category, the aging deviation, the degradation indexes, the water-leakage generation frequency, the correlation with disturbance energy, and the like are stored and accumulated in the SDB 121. The abnormality determination result detection and the degradation evaluation, by measurement of only single target, are realistically impossible because of requirement of a lapse of decades. Therefore, a water-leakage generation frequency (e.g., case/100 km/year) is statistically determined from past water-leakage records (Step SC11). Moreover, as a cause of water-leakage, there is a surrounding load application (vehicle driving vibration and the like). Thus, vibration data per unit time measured randomly in daytime and nighttime are subjected to integration processing. By this process, disturbance energy of each target pipeline is determined (Step SB1). Afterward, in the step SB2, numerical values of degradation indexes (the number of years, outputs) with respect to the magnitude of the disturbance energy are organized in a table or a graph. By the organization results, an approximate formula is expressed by a mathematical formula if possible (Statistical calculation processing).

Subsequently, in the step SA4, the possible abnormality evaluation analyzed with respect to the measurement data of the vibration measurement device(s) arranged in each pipeline, an evaluation by the degradation indexes determined by the statistical calculation processing unit 12, and an evaluation by the disturbance energy index are performed. Afterward, in the step SA5, with respect to the measurement results exceeding previously-set certain conditions (Yes), a water-leakage alarm and a degradation alarm are activated (Step SA6), and the measurement results are output by the information output section 115 (Step SA8). Furthermore, in the step SA7, on the basis of the measurement results, the corresponding soundness is determined Afterward, in the step SA9, the results of the water-leakage determination, the degradation abnormality determination, and the soundness determination are stored and accumulated in the MDB 112. Furthermore, in the step SA10, degradation diagnostic information including the soundness is reflected in the asset management system 5 (Private data processing).

When there is a pipeline with an unknown installation year due to an error in the pipeline database, the installation year is estimated through determination of the predicted number of elapsed years by comparing the aging characteristic graph prepared according to the diameter that is a pipeline attribute category and the vibration measurement values of a target pipeline in the step SD1. Afterward, in the step SD2, the estimated installation year is reflected in the attribute data on the MDB 112.

In the step SD3, by repeatedly performing labeling based on measurement results (labeling by input processing to aging characteristics categorized according to the diameter that is a pipeline attribute category, an update of the labeling by input processing to the disturbance energy evaluation) or reconsidering and updating setting of the conditions for the alarm determination, the accuracy of the water-leakage detection, the degradation prediction, and the soundness evaluation can be improved (Statistical calculation processing).

In the detection of abnormality such as a water-leakage or the like and the degradation prediction, as in the present embodiment, the determination accuracy can be further improved by connecting, for example, measurement device(s) such as a flow rate measurement device(s) and the like in addition to the vibration measurement device(s). For these measurement device(s), a method capable of attaching these measurement device(s) afterward without requiring boring a pipe component of a pipeline and processing such as cutting and the like can be used. For example, an ultrasonic flow rate measurement device(s) is arranged adjacent to the upstream side(s) of a vibration measurement device(s) (the number of the flow rate measurement devices to be arranged can be less than the vibration measurement device(s)) and measures a flow rate. In the case of an increase in flow rate in a time period in which a water supply is less utilized such as early morning and midnight or an increase in total flow rate in a certain period of time, a possibility of water-leakage is increased. In contrast, when the flow rate is reduced, degradation due to narrowing a flow path by scale adhesion/deposition and the like is expected. The measurement device(s) is used considering the concerns of reduction in accuracy due to air bubbles, contaminations, and the like.

Next, a reflection of the water-leakage determination and the like in the asset management system 5 is described with reference to an example. The hazard of each pipeline considering factors of the environmental conditions is considered. For example, a diameter correction coefficient, a liquefaction correction coefficient, and a standard damage ratio by earthquake intensity of each pipeline to be managed are considered and set to determine the hazard on the basis of conventionally known references and documents such as the "conference report on earthquake resistance of pipeline" (Ministry of Health, Labour and Welfare, Conference of earthquake resistance of pipeline) and the "technical research and development report on prediction and search for damage to water supply by earthquake" (Japan Water Research Center). Mapping of a pipeline database is superimposed on a hazard map in which prediction of a liquefaction area and earthquake intensity by area are performed to set the liquefaction correction coefficient and the standard damage ratio by earthquake intensity, of each target pipeline.

By linking with the asset management system 5, a replacement plan is considered. The asset management can be performed with reference to, for example, the "instruction regarding asset management in water supply business" (Ministry of Health, Labour and Welfare). The priority for replacement of pipeline to be managed is set on the basis of the soundness determination and the hazard determination based on the measurement results of each pipeline, a replacement demand outlook is developed on the basis of the estimation of life cycle cost of each pipeline, and the operable medium- to long-term replacement plan (including a repair and an implementation method) and the operable medium- to long-term investment plan are developed by comparing with the fiscal balance outlook.

INDUSTRIAL APPLICABILITY

As described above, according to the present invention, a pipeline management supporting server and a pipeline management supporting system, capable of unifying management of attribute data of a pipe component and location information on a pipe network, efficiently detecting an abnormality of a pipeline remotely, and diagnosing the degradation state of the pipeline, can be provided. Although the case where the pipeline to be managed is a water supply pipeline is specifically described in the embodiment, the pipeline to be managed in the present invention is not limited to the water supply pipeline, and the present invention is applicable to a wide range of field such as pipeline networks of plants and energy-related facilities such as pipelines of oil and gas and the like.

While the invention has been particularly shown and described with reference to the exemplary embodiment thereof, the invention is not limited to the embodiment. It will be understood by those of ordinary skill in the art that various changes in form and details may be made therein without departing from the spirit and scope of the present invention as defined by the claims.

This application is based upon and claims the benefit of priority from Japanese patent application No. 2012-083205, filed on Mar. 30, 2012, the disclosure of which is incorporated herein its entirety by reference.

EXPLANATION OF REFERENCE NUMERALS 1 pipeline management supporting server
2 management center
3 field
4 communication network
5 asset management system
11 private data processing unit
12 statistical calculation processing unit
21 mobile terminal (data collection transmission terminal)
22 fixed relay station (data collection transmission terminal)
31 vibration sensor (sensor)
32 flow rate sensor (sensor)
40 water supply pipeline
41 manhole
51 operation display device
111 pipeline database data storage section (PDB)
112 measured event data storage section (MDB)
113 possible abnormality detection section
114 event data acquisition section
115 information output section
121 statistical calculation data storage section (SDB)
122 data analysis section
123 calculation processing correction section
131 asset management database data storage section (AMDB)

The invention claimed is:

1. A pipeline management supporting server comprising:
a private data processing unit; and
a statistical calculation processing unit,
wherein the private data processing unit comprises memory and a processor configured to:
acquire event data of a pipeline measured by at least one sensor, wherein the at least one sensor comprises at least one of a vibration sensor and a flow rate sensor, and the event data comprises at least one of vibration data and flow rate data;
store the event data of the pipeline;
identify a pipeline and a location pertaining to the acquired event data of the pipeline with reference to pipeline database data; and
generate possible abnormality detection information on the acquired event data of the pipeline,
wherein the statistical calculation processing unit comprises memory and a processor configured to:
prepare, from event data of plural pipelines each having the same attribute as the pipeline pertaining to the event data acquired by the private data processing unit, an aging characteristic graph of the plural pipelines; and
generate degradation state diagnostic information on the pipeline pertaining to the event data acquired by the private data processing unit based on the acquired event data and the aging characteristic graph,
wherein the processor in the private data processing unit is further configured to generate abnormality determination result detection information based on a comparison of the generated possible abnormality detection information and the generated degradation state diagnostic information.

2. The pipeline management supporting server according to claim 1, wherein as substitute for generating an aging characteristic graph, the statistical calculation processing unit:
stores a previously-prepared aging characteristic graph of pipelines each having the same attribute as the pipeline pertaining to the event data acquired by the private data processing unit, and
generates degradation state diagnostic information on the pipeline pertaining to the event data acquired by the private data processing unit based on the acquired event data and the previously-prepared aging characteristic graph.

3. The pipeline management supporting server according to claim 1, wherein
the processor in the statistical calculation processing unit is further configured to update the aging characteristic graph on the basis of the acquired event data.

4. The pipeline management supporting server according to claim 3, wherein
the processor in the statistical calculation processing unit is further configured to extract disturbance energy data included in the event data and prepare a disturbance energy characteristic graph on the basis of the disturbance energy data.

5. The pipeline management supporting server according to claim 1, wherein the generated degradation state diagnostic information is at least one of degradation index evaluation information and soundness index evaluation information on the pipeline.

6. The pipeline management supporting server according to claim 1, wherein
the pipeline to be managed is a water supply pipeline.

7. A pipeline management supporting system comprising:
a pipeline management supporting server;
at least one sensor;
an operation display device;
at least one data collection transmission terminal; and
a communication network, wherein
the pipeline management supporting server is the pipeline management supporting server according to claim 1,
event data measured by the at least one sensor are sent to the pipeline management supporting server by the at least one data collection transmission terminal through the communication network, and
abnormality determination result detection information and degradation state diagnostic information output from the pipeline management supporting server are acquirable by the operation display device via the communication network.

* * * * *